US010605784B2

(12) United States Patent
Bar-Cohen et al.

(10) Patent No.: US 10,605,784 B2
(45) Date of Patent: *Mar. 31, 2020

(54) HIGH TEMPERATURE ULTRASONIC PROBE AND PULSE-ECHO PROBE MOUNTING FIXTURE FOR TESTING AND BLIND ALIGNMENT ON STEAM PIPES

(71) Applicant: CALIFORNIA INSTITUTE OF TECHNOLOGY, Pasadena, CA (US)

(72) Inventors: Yoseph Bar-Cohen, Seal Beach, CA (US); Mircea Badescu, La Canada Flintridge, CA (US); Shyh-Shiuh Lih, La Canada Flintridge, CA (US); Stewart Sherrit, La Crescenta, CA (US); Nobuyuki Takano, Arcadia, CA (US); Patrick N. Ostlund, Pomona, CA (US); Hyeong Jae Lee, South Pasadena, CA (US); Xiaoqi Bao, San Gabriel, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 513 days.

This patent is subject to a terminal disclaimer.

(21) Appl. No.: 15/413,237

(22) Filed: Jan. 23, 2017

(65) Prior Publication Data

US 2017/0131241 A1    May 11, 2017

Related U.S. Application Data

(63) Continuation of application No. 14/259,893, filed on Apr. 23, 2014, now Pat. No. 9,586,234.

(Continued)

(51) Int. Cl.
*H01L 41/053* (2006.01)
*G01N 29/22* (2006.01)
(Continued)

(52) U.S. Cl.
CPC ......... *G01N 29/223* (2013.01); *B06B 1/0215* (2013.01); *B06B 1/0644* (2013.01);
(Continued)

(58) Field of Classification Search
CPC .................................................... H01L 41/053
See application file for complete search history.

(56) References Cited

U.S. PATENT DOCUMENTS 7,360,403 B2 * 4/2008 Jones ..................... G01N 15/02
                                                              73/61.75
9,586,234 B2 * 3/2017 Bar-Cohen ............ B06B 1/0644

* cited by examiner

*Primary Examiner* — Thomas M Dougherty
*Assistant Examiner* — Karen B Addison
(74) *Attorney, Agent, or Firm* — Steinfl + Bruno LLP

(57) ABSTRACT

A high temperature ultrasonic probe and a mounting fixture for attaching and aligning the probe to a steam pipe using blind alignment. The high temperature ultrasonic probe includes a piezoelectric transducer having a high temperature. The probe provides both transmitting and receiving functionality. The mounting fixture allows the high temperature ultrasonic probe to be accurately aligned to the bottom external surface of the steam pipe so that the presence of liquid water in the steam pipe can be monitored. The mounting fixture with a mounted high temperature ultrasonic probe are used to conduct health monitoring of steam pipes and to track the height of condensed water through the wall in real-time.

21 Claims, 15 Drawing Sheets

Related U.S. Application Data

(60) Provisional application No. 61/815,110, filed on Apr. 23, 2013, provisional application No. 61/815,191, filed on Apr. 23, 2013.

(51) Int. Cl.
| | | |
|---|---|---|
| *B06B 1/06* | (2006.01) | |
| *B06B 1/02* | (2006.01) | |
| *G01N 29/24* | (2006.01) | |
| *B06B 3/00* | (2006.01) | |
| *G01F 23/296* | (2006.01) | |

(52) U.S. Cl.
CPC ............ *B06B 3/00* (2013.01); *G01F 23/2962* (2013.01); *G01N 29/228* (2013.01); *G01N 29/2437* (2013.01); *H01L 41/053* (2013.01); *G01N 2291/011* (2013.01); *G01N 2291/044* (2013.01); *G01N 2291/101* (2013.01)

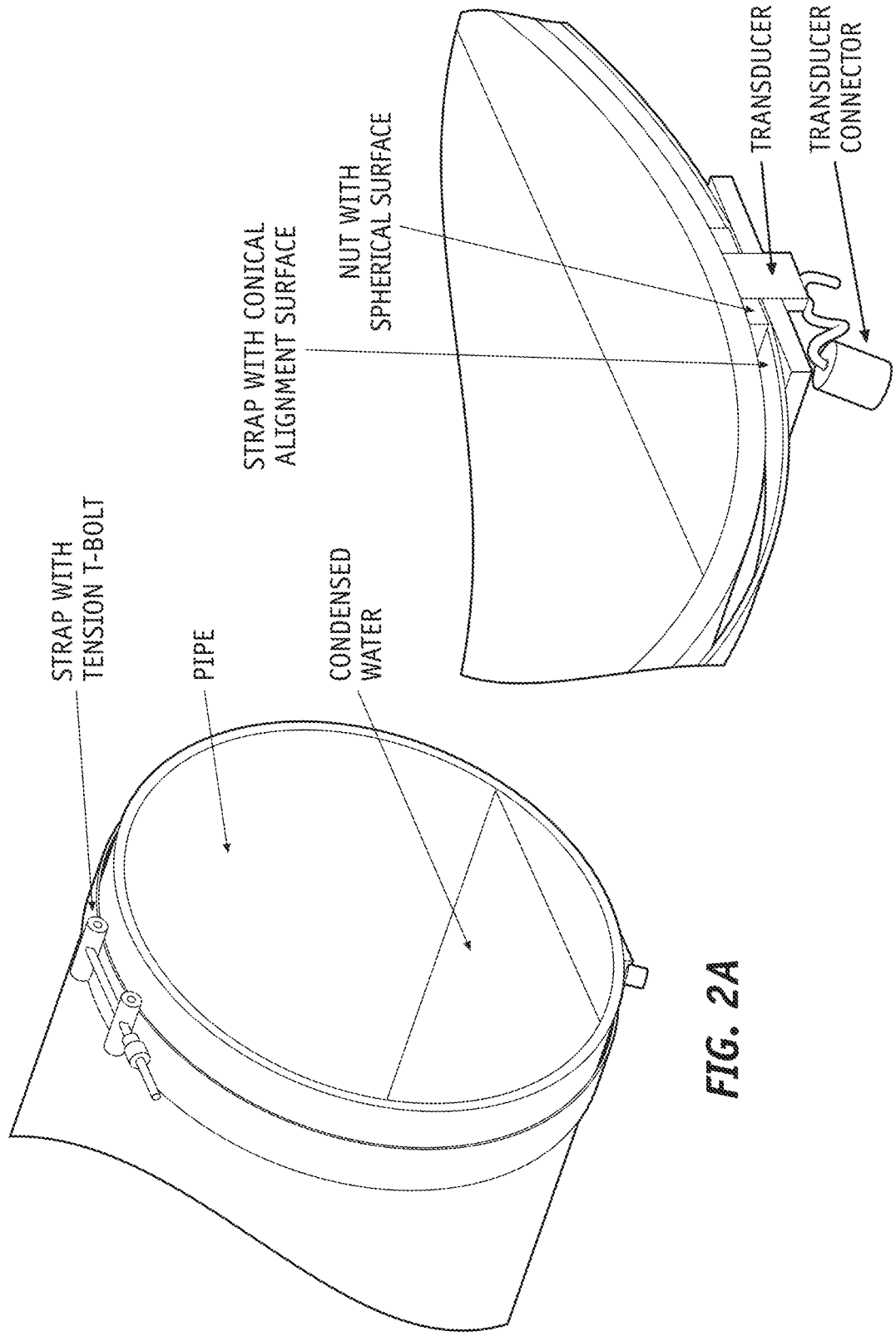

HIGH TEMPERATURE ULTRASONIC PROBE AND PULSE-ECHO PROBE MOUNTING FIXTURE FOR TESTING AND BLIND ALIGNMENT ON STEAM PIPES

CROSS REFERENCE TO RELATED APPLICATIONS

The present application is a Continuation of U.S. patent application Ser. No. 14/259,893 filed Apr. 23, 2014, which in turn, claims priority to and benefit of U.S. provisional patent application Ser. No. 61/815,110 filed Apr. 23, 2013, and priority to and the benefit of U.S. provisional patent application Ser. No. 61/815,191, filed Apr. 23, 2013, each of which applications is incorporated herein by reference in its entirety.

STATEMENT REGARDING FEDERALLY FUNDED RESEARCH OR DEVELOPMENT

The invention described herein was made in the performance of work under a NASA contract, and is subject to the provisions of Public Law 96-517 (35 USC 202) in which the Contractor has elected to retain title.

FIELD OF THE INVENTION

The invention relates to ultrasonic measurements in general and particularly to systems and methods that provide ultrasonic measurements on pipes.

BACKGROUND OF THE INVENTION

Water condensation in steam pipes can lead to potential accidents and system failures in a steam pipe system.

One of the concerns to such a system is the excitation of water hammer that may lead to serious consequences including damaged vents, traps, regulators and piping. The water hammer is caused by accumulation of condensed water that is trapped in a portion of horizontal steam pipes. The fast flowing steam over the condensed water causes ripples in the water creating buildup of turbulence and resulting in the water formation of a solid mass or slug that fills the pipe. The slug of the condensed water can travel at the speed of the steam striking the first elbow that is encountered in its path. The force can be comparable to a hammer blow and can be sufficiently large to break the back of the elbow.

There is a need for monitoring systems and methods that sustains the conditions next to a steam pipe to be monitored in real time.

SUMMARY OF THE INVENTION

According to one aspect, the invention features a high-temperature ultrasonic probe. The high-temperature ultrasonic probe comprises a piezoelectric transducer element having a Curie temperature of at least 350° C. and a mechanical damping (tan δ) of 0.02 or less; electrical input terminals configured to receive a driving signal to the piezoelectric transducer element; electrical output terminals configured to provide a response signal from the piezoelectric transducer element; a preload flexure; and a probe housing.

In one embodiment, the high-temperature ultrasonic probe is configured to perform pulse-echo measurements at a frequency of 2.25 MHz or higher.

In another embodiment, the ultrasonic probe is configured to act as both an ultrasonic transmitter and an ultrasonic receiver.

In yet another embodiment, the high-temperature ultrasonic probe further comprises a backing.

In still another embodiment, the backing is configured to reduce the duration of a ringing in the piezoelectric probe element.

In a further embodiment, the backing is a selected one of air, a high impedance polymer and a low impedance polymer.

In yet a further embodiment, the high-temperature ultrasonic probe further comprises a preload offset.

In an additional embodiment, the high-temperature ultrasonic probe further comprises a pulser/receiver and amplifier.

In one more embodiment, the high-temperature ultrasonic probe further comprises a digital signal processor.

In still a further embodiment, the high-temperature ultrasonic probe further comprises a wireless communication module.

According to another aspect, the invention relates to a mounting fixture for attaching a high-temperature ultrasonic probe to a steam pipe. The mounting fixture comprises a frame; a probe alignment guide connected to the frame by way of a plurality of flexures; two strap pins attached to the frame; three alignment bolts attached to the frame; and a strap.

In one embodiment, the probe alignment guide is configured to determine an axis of a high-temperature ultrasonic probe.

In another embodiment, the plurality of flexures are configured to keep the high-temperature ultrasonic probe in contact with the steam pipe.

In another embodiment, the plurality of flexures are configured to keep the orientation of the probe alignment guide constant while preloading the probe against the pipe and through temperature variations of the pipe and environment.

In yet another embodiment, the strap pins contain a spherical surface for strap pin mounting.

In still another embodiment, the strap pins comprise a selected one of a pin joint, a ball joint and a sliding ball joint.

In a further embodiment, the three alignment bolts each have a sharp end.

In yet a further embodiment, the three alignment bolts are configured to be independently adjusted to align the mounting fixture relative to a local preferred direction.

In still a further embodiment, the local preferred direction is a local vertical direction.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 2A is a perspective view of the mounting strap for the alignment and strapping the probe to the pipe surface in the field.

FIG. 2B is a perspective view of the mounting strap for the alignment and strapping the probe to the pipe surface in the field.

DETAILED DESCRIPTION

The problem that was addressed is the need to prevent failures in aging steam pipe systems found in many places. An effective in-service health monitoring system is needed to track water condensation in real-time through the wall of the steam pipes. The system is required to measure the height of the condensed water from outside the pipe while operating at temperatures that are as high as 250° C. The system needs to account for the effects of water flow and cavitation. In addition, it is desired that the system does not require perforating the pipes and thereby reducing the structural integrity.

We describe an alignment fixture that allows for the blind alignment of ultrasonic pulse-echo probes for mounting on pipes. The strap with a mounted probe is used to conduct health monitoring of steam pipes and track the height of condensed water through the wall in real-time.

The novel features of this disclosure are believed to include a novel mounting fixture design that allows alignment of ultrasonic pulse-echo probe onto pipes, and a mounting fixture that allows for alignment of pulse-echo probes without the use of reference reflection from condensed water in steam pipes while testing thru the wall of the pipe.

The disclosed mounting fixture can be used for testing that involves ultrasonic pulse-echo testing of pipes. We identified materials that can sustain performance at high temperatures that enable this invention.

The ultrasonic pulse-echo probe can sustain temperatures as high as 250° C. It uses a piezoelectric transducer to generate and receive the ultrasonic pulses. The transducer is made of a material with high Curie temperature (denoted by $T_C$) and the probe is configured such that it is operated as an air-backed transducer that has minimum losses of power. The probe needs to be mounted in a manhole under high humidity (80%) and temperature conditions (higher than 70° C.). Under conventional procedures, the high temperature of the pipe cures the currently used couplant (or adhesive) in seconds. This does not allow fine adjustment of the probe orientation. The fixture that is described allows for the alignment of the mounting fixture first and then insertion and preloading of the probe without the need to perform further alignment. The feasibility of the disclosed mounting fixture was demonstrated in the lab.

The probe and its mounting fixture are important parts of a health monitoring of steam pipes that is being developed. A high temperature piezoelectric transducer generates and receives ultrasonic waves. In a preferred embodiment, the probe transmits the wave normal to the pipe surface. The mounting fixture was designed to allow for alighment of the probe even without a reference reflection and thus enables "blind" alignment. An illustration of the health monitoring system for which the probe and the alignment fixture were developed is shown in FIG. 1.

Figure 1:
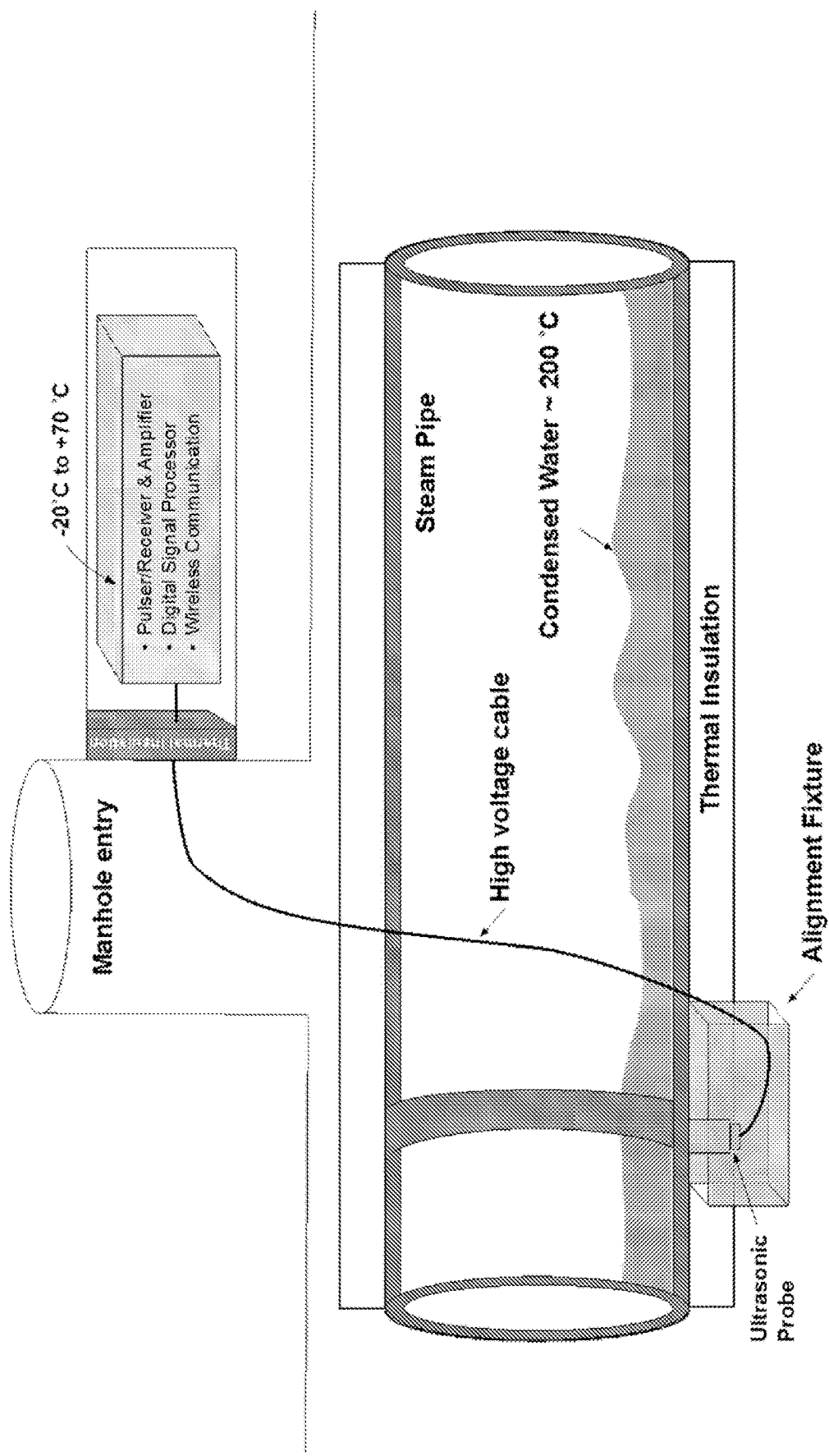
FIG. 1 is a diagram that illustrates the health monitoring system and the pulse echo method of measuring the condensed water height in a steam pipe using time-of-flight of reflected ultrasonic waves.

FIG. 1 is a diagram that illustrates the health monitoring system and the pulse echo method of measuring the condensed water height in a steam pipe using time-of-flight of reflected ultrasonic waves.

In order to allow aligning the probe normal to the surface of potential water condensation and to secure intimate contract to the pipe surface a novel mounting fixture was conceived and developed.

FIG. 2A is a perspective view of the mounting strap for the alignment and strapping the probe to the pipe surface in the field.

FIG. 2B is a perspective view of the mounting strap for the alignment and strapping the probe to the pipe surface in the field.

Figure 2C:
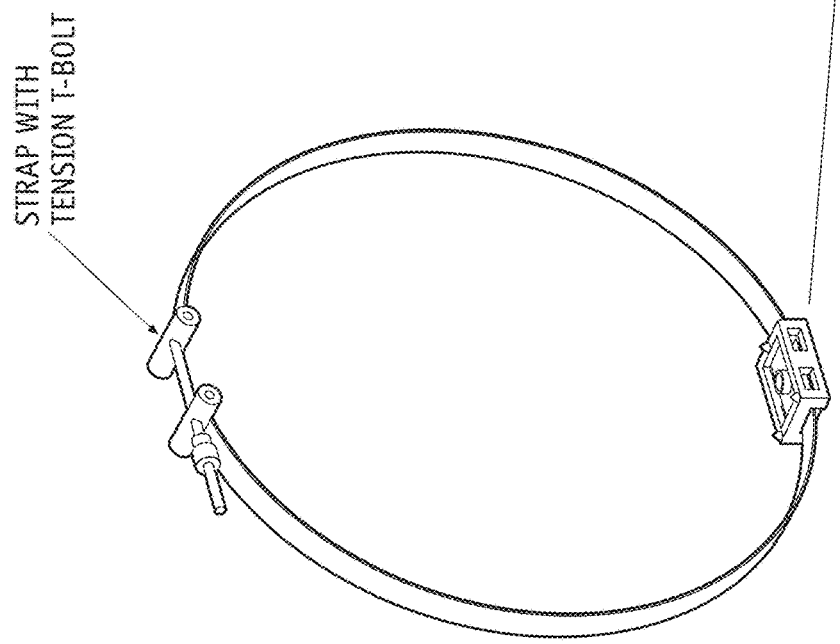
FIG. 2C is a perspective view of the mounting strap for the alignment and strapping the probe to the pipe surface in the field.

FIG. 2C is a perspective view of the mounting strap for the alignment and strapping the probe to the pipe surface in the field.

Figure 2D:
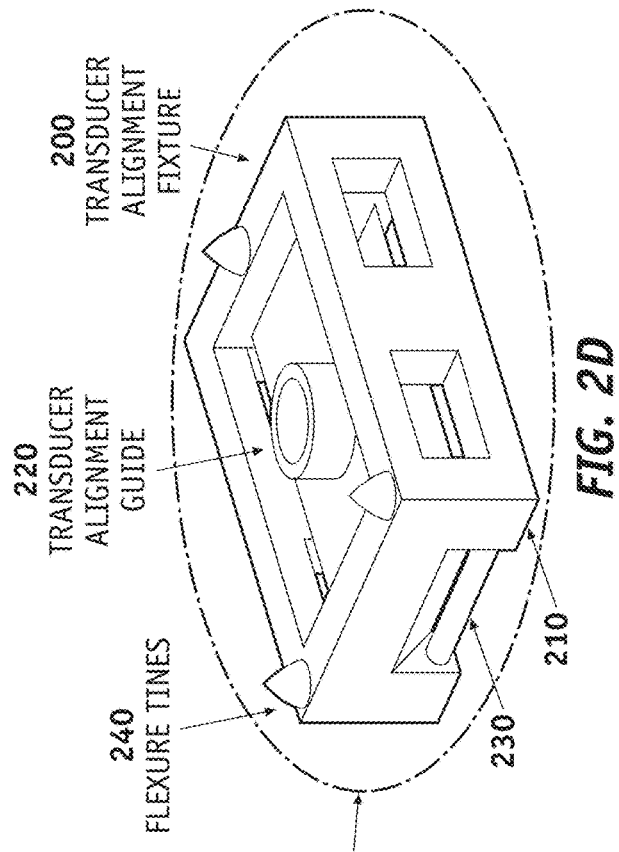
FIG. 2D is a perspective view of the probe alignment fixture.

FIG. 2D is a perspective view of the probe alignment flexure.

Figure 2E:
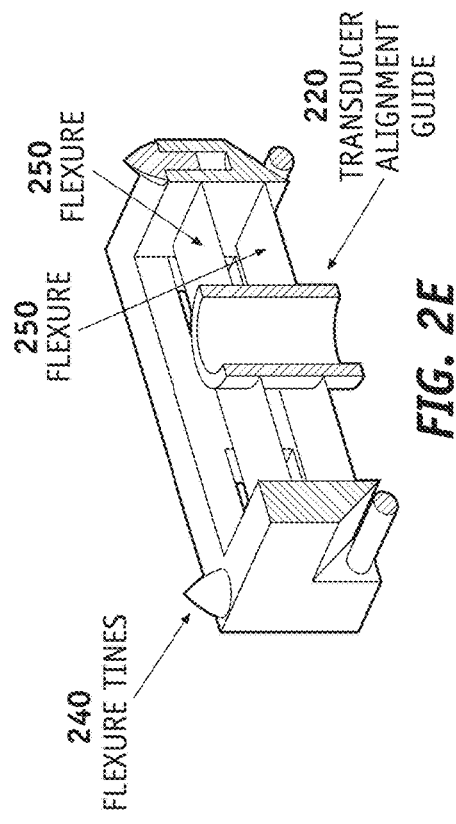
FIG. 2E is a cutaway view of the probe alignment fixture.

FIG. 2E is a cutaway view of the probe alignment guide.

Figure 3A:
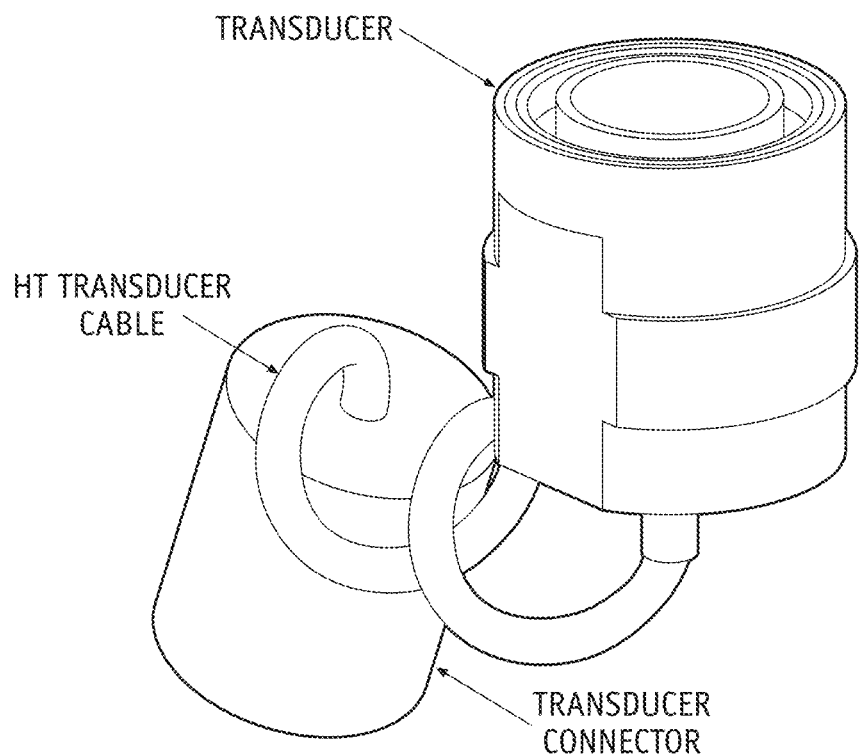
FIG. 3A is a perspective view of the probe and the connection fixture for the mounting in the field.

FIG. 3A is a perspective view of the probe and the connection fixture for the mounting in the field.

Figure 3B:
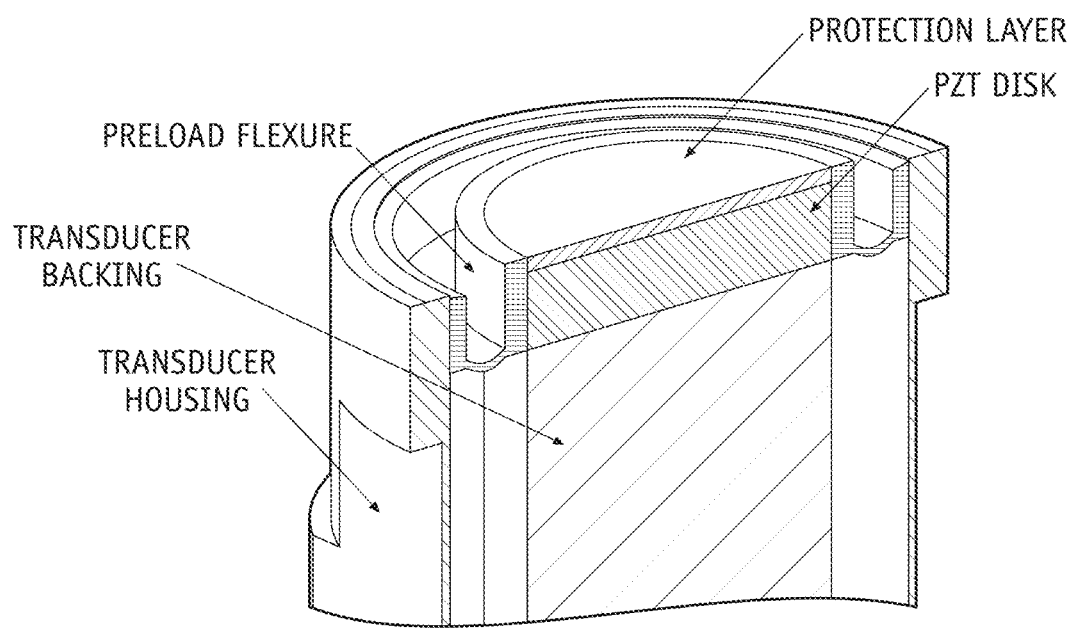
FIG. 3B is a sectional view through the probe.

FIG. 3B is a sectional view through the probe.

Figure 3C:
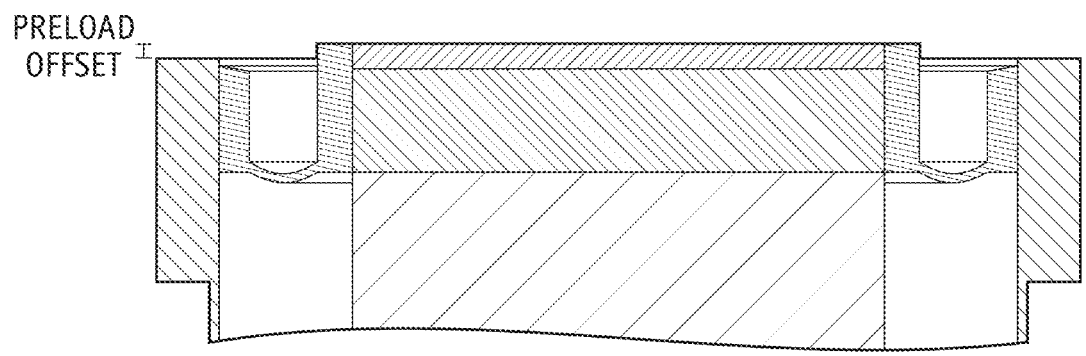
FIG. 3C is a cross-sectional plan view showing the pre-load offset.

FIG. 3C is a cross-sectional plan view showing the preload offset.

Figure 4A:
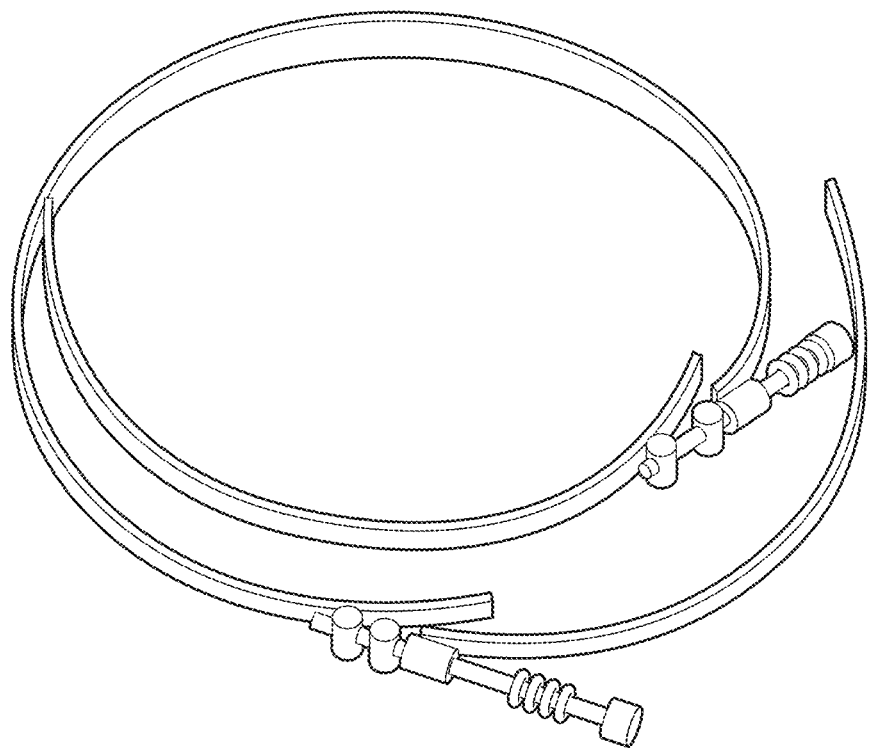
FIG. 4A is an image of the pipe mounting strap elements.

FIG. 4A is an image of the pipe mounting strap elements.

Figure 4B:
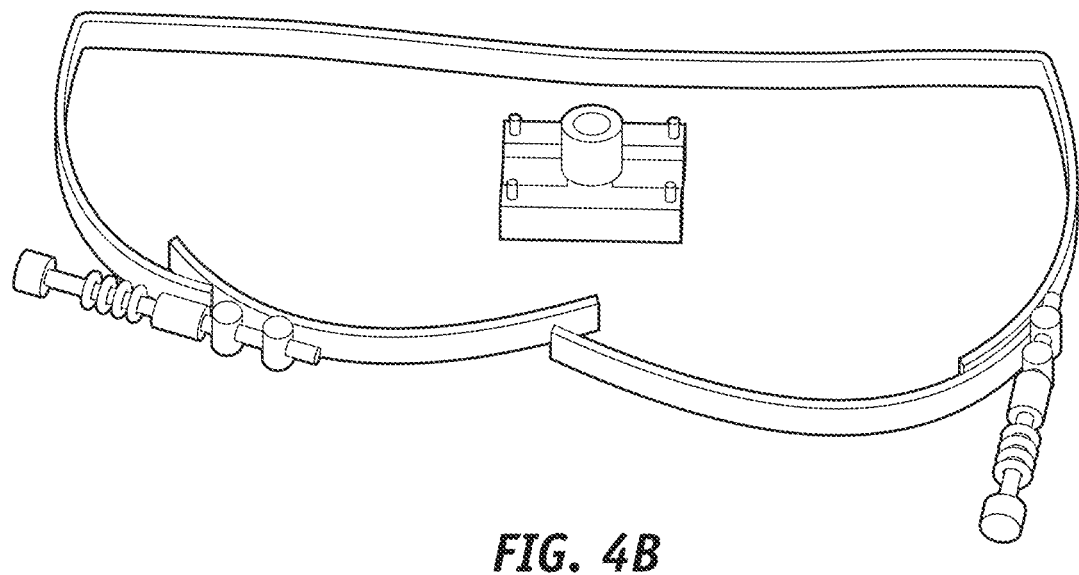
FIG. 4B is an image of the pipe mounting strap elements and the half pipe mounting strap and block.

FIG. 4B is an image of the pipe mounting strap elements and the half pipe mounting strap and block.

Figure 5:
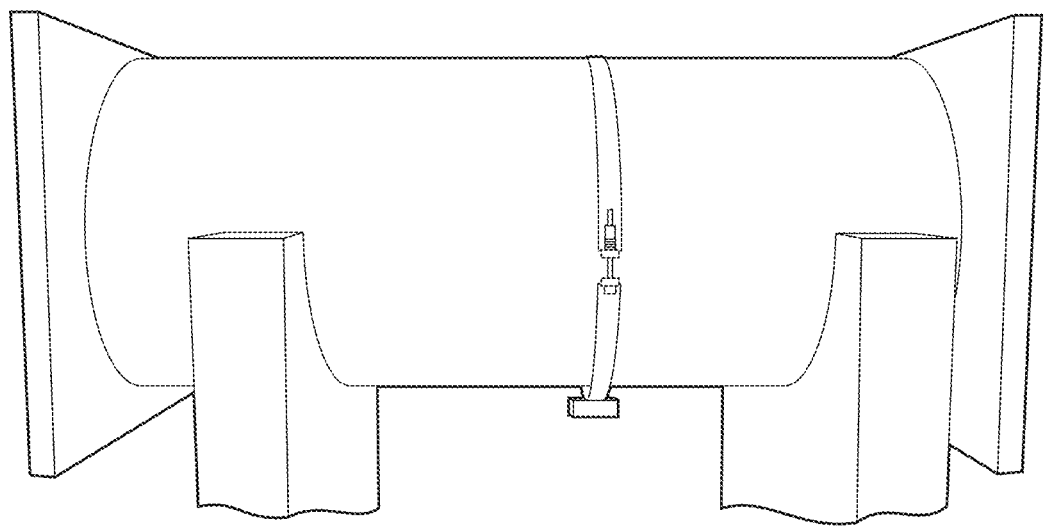
FIG. 5 is an image of a mockup of a steam pipe with the strap and the probe attached simulating operation in the field.

FIG. 5 is an image of a mockup of a steam pipe with the strap and the probe attached simulating operation in the field.

The pipe mount fixture comprises a probe alignment fixture and a strap. The strap includes a tension T-bolt with a spring for maintaining the tension in the strap even with large temperature variations and a coefficient of thermal expansion mismatch between the material of the steam pipe and the strap material. The strap keeps the alignment fixture pressed against the pipe. The alignment fixture 200 includes a frame 210, a probe alignment guide 220, two strap pins 230 and three alignment bolts 240. The probe alignment guide 220 determines the axis of the probe and is attached to the frame through parallel flexures 250. The flexures 250 maintain the guide alignment with respect to the fixture 200 and keep the probe in contact with the pipe. The strap pins 230 allow the strap ends to be attached to the alignment fixture 200 and contain a spherical surface for strap pin mounting. The three alignment bolts 240 each have a sharp end. Their position in the alignment fixture can be independently adjusted to align the fixture relative to the local vertical direction. The process of mounting the probe to the pipe comprises the following two steps:

Step 1: Attach the strap to the pipe and orient the probe alignment flexure to the local vertical direction.

Step 2: Apply the bonding material onto the probe face, insert the probe into the guide, press against the pipe and preload and secure the probe backing against the alignment guide.

When the health monitoring system is installed in the manhole, it is important to be able to align the probe without the presence of water surface inside the pipe. For this purpose, the mounting fixture was designed to allow for blind alignment capability. Three design options that would allow for circumferential alignment as shown in FIG. 6.

Figure 6A:
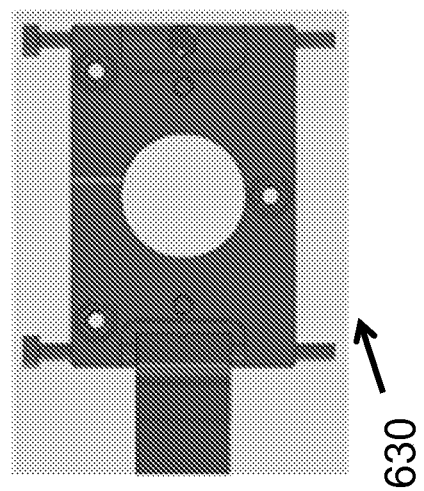
FIG. 6A is an image of a sliding ball joint for attaching the mounting strap.

FIG. 6A is an image of a sliding ball joint 610 for attaching the mounting strap.

Figure 6B:
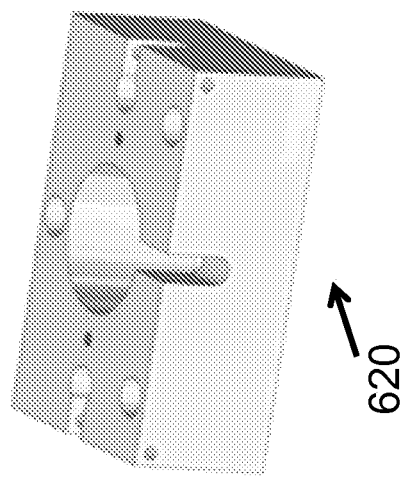
FIG. 6B is an image of a ball joint for attaching the mounting strap.

FIG. 6B is an image of a ball joint 620 for attaching the mounting strap.

Figure 6C:
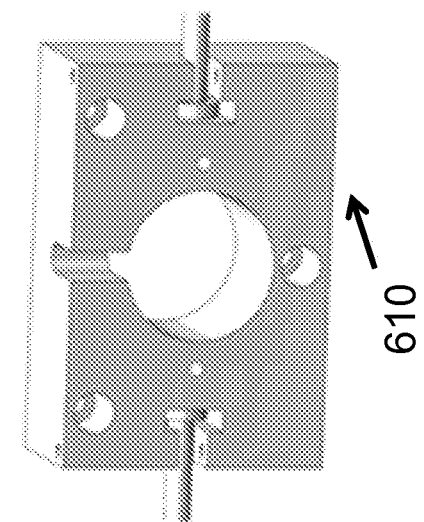
FIG. 6C is an image of a pin joint for attaching the mounting strap.

FIG. 6C is an image of a pin joint 630 with a spherical crowned surface for attaching the mounting strap.

After assessing the capability of these three designs the one that we chose is the configuration that is shown in FIG. 6A. It comprises a ball joint and slide.

Figure 7A:
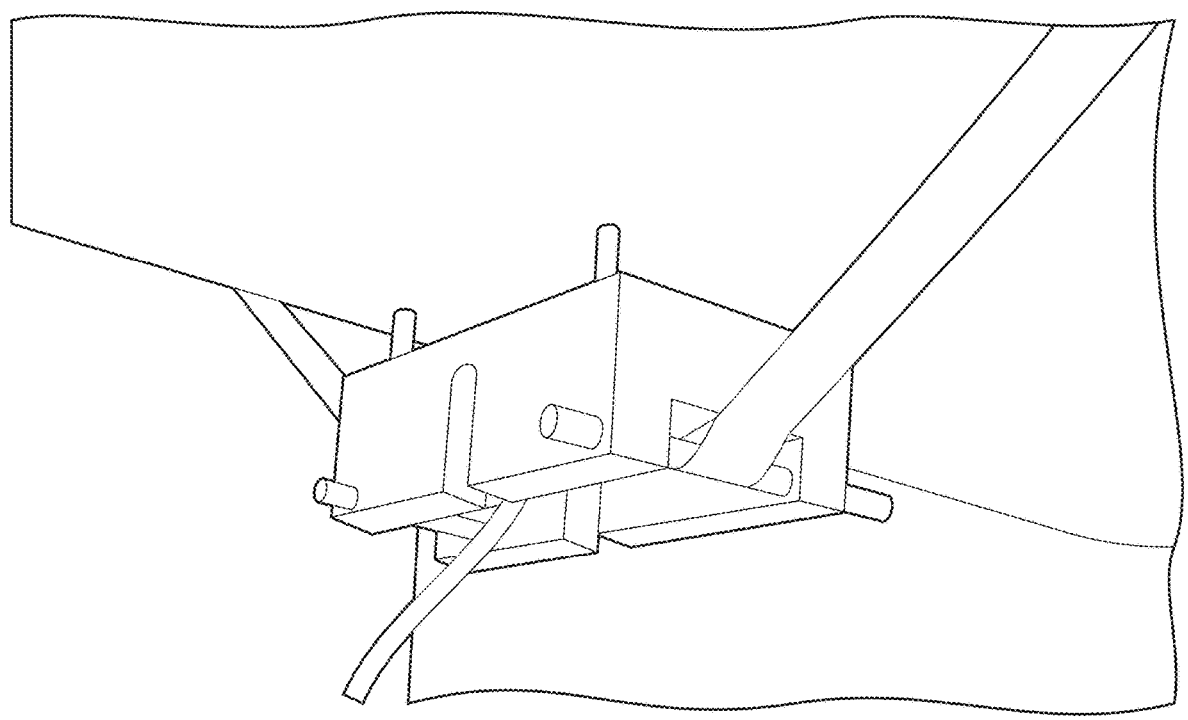
FIG. 7A is an image of a strap that has restricted circumferential alignment capability.
Figure 7B:
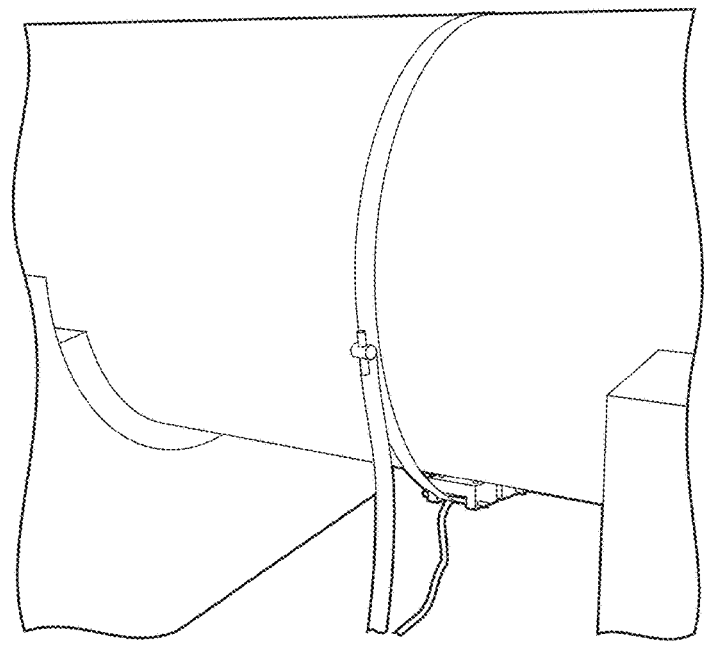
FIG. 7B is another image of the strap shown in FIG. 7A.

The fixture was manufactured and is shown in FIG. 7A and FIG. 7B. FIG. 7A is an image of a strap that has restricted circumferential alignment capability. FIG. 7B is another image of the strap shown in FIG. 7A.

Figure 8:
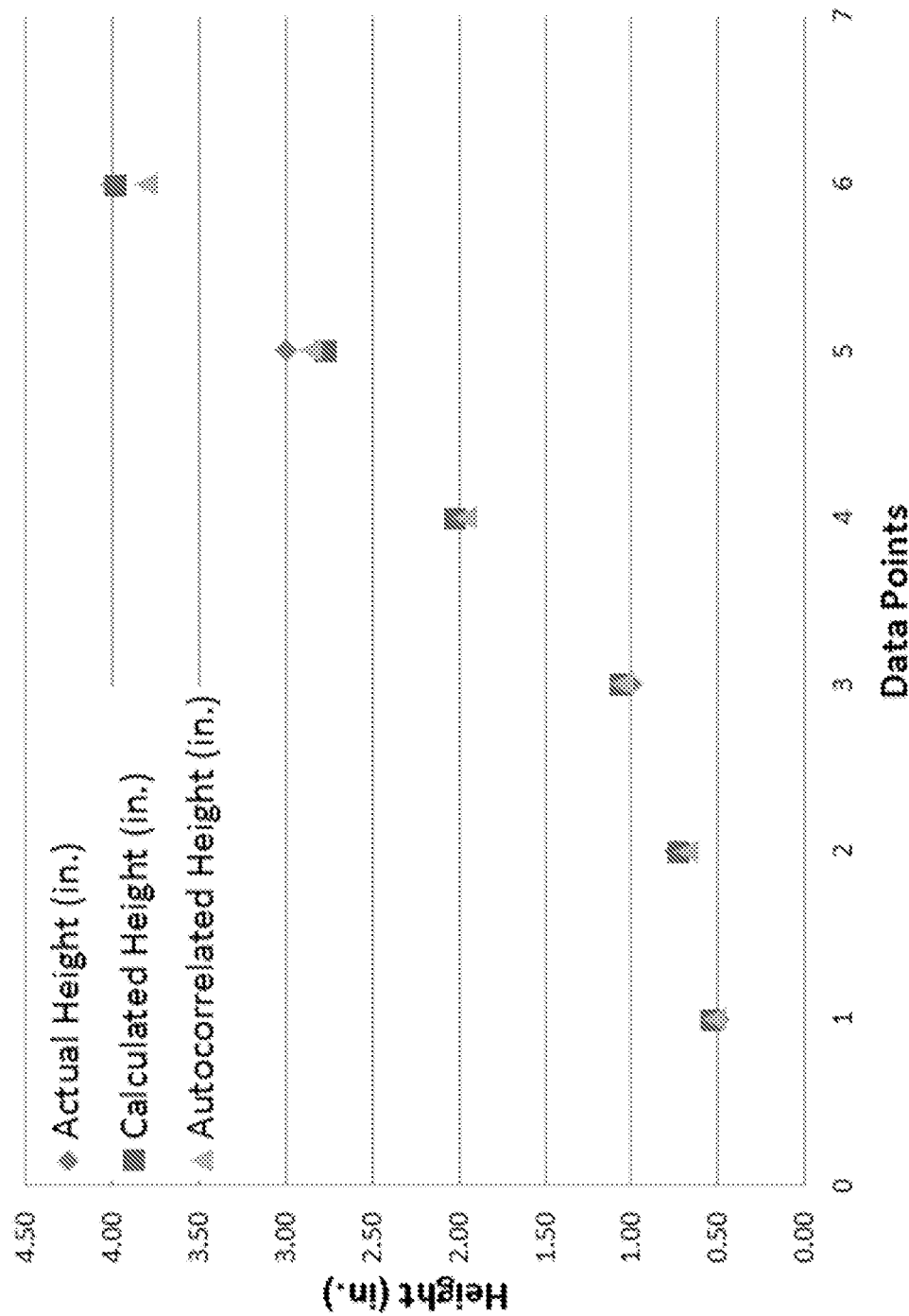
FIG. 8 is a graph of the measured height of water in the simulation pipe using a strapped probe at room temperature, with the actual height also indicated.

Tests were made with the strap mounted on the pipe section and the probe was blindly aligned. Water was added gradually into the pipe and measurements were performed at every 0.25 inch until the water height reached 1 inch, then the height was increased by 1 inch each time. Using autocorrelation and a Hilbert transform the reflections from the 1 inch and higher were resolved quite easily. The highest water surface reflection that was detected was at 9.375 inches and this proved the success of the fixture capability. Determination of the height below 1 inch is accomplished by reducing the signal duration (e.g., transmit shorter signals) which improves the probe resolution. Using the signal analysis algorithms and the probe (made by NDT Transducers) at room temperature, the strapped probe performance was tested. The results are quite promising as shown in FIG. 8.

We now describe a high temperature ultrasonic pulse-echo probe that can sustain exposure to as high as 250° C. The probe was developed for measuring in real-time the height of condensed water through the wall of a steam pipe as part of a health monitoring system.

The ultrasonic pulse-echo probe allows for testing pipes at high temperatures for nondestructive evaluation (NDE) and health monitoring applications. The development of this probe was motivated by the observation that no commercial probe that is reliable has been found in spite of numerous internet searches and company contacts. We identified materials that can sustain performance at high temperatures that supports this invention.

An effective in-service health monitoring system is needed to track water condensation in real-time through the wall of a steam pipes. The system preferably is capable of measuring the height of the condensed water from outside the pipe while operating at temperatures that are as high as 250° C. The system preferably needs to be able to account for the effects of water flow and cavitation. In addition, it is desired that the system does not require perforating the pipes and thereby reducing their structural integrity.

Figure 9:
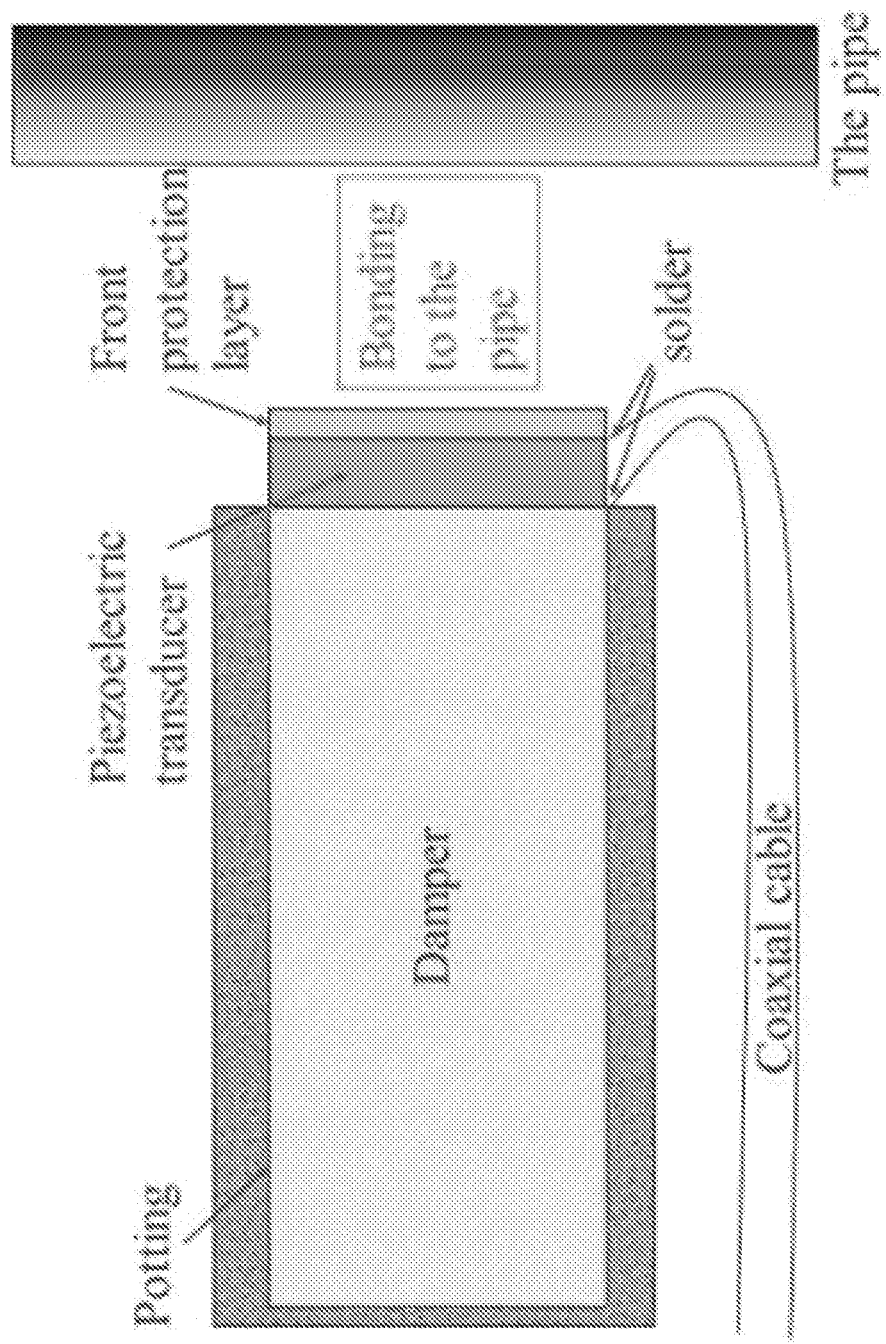
FIG. 9 is a schematic diagram illustrating the probe components (not to scale).

The probe is an important part of a health monitoring of steam pipes. An illustration of the health monitoring system for which the probe was developed is shown in FIG. 1. The general configuration of an ultrasonic probe is schematically shown in FIG. 9.

A piezoelectric transducer is an important component in this ultrasonic system. It acts as both an ultrasonic transmitter and an ultrasonic receiver. The relevant figure of merit of the piezoelectric transducer is electromechanical coupling factor as high-coupling piezoelectrics allow effective energy conversion in both transmitting and receiving energy, improved bandwidth and sensitivity of the probe response. For use of the piezoelectric transducers at high temperature, other aspects need to be considered, such as phase transition, thermal aging, electrical resistivity, chemical stability (decomposition and defect creation), and the stability of properties at elevated temperatures. Among these considerations, the phase transition at elevated temperature is the most important limitation as the transducer is permanently depolarized at a certain temperature, known as the Curie point or Curie temperature, and cannot be used for transducer applications without being repoled. Although the piezoelectric materials that possess high Curie points greater than 500° C. are available, such as bismuth layer structured ferroelectric (BLSF), lithium niobate ($LiNbO_3$) and Quartz, their transducer properties are considerably lower than conventional piezoelectric material, such as lead zirconate titanate (PZT). In particular, the health monitoring system working at high temperature (higher than 200° C., and preferably higher than 250° C.) requires high performance piezoelectric transducers. Some of the factors that preferably should be taken into account include the effect of the pipe wall curvature that causes ultrasonic wave losses and increased attenuation at high temperatures. These effects can appreciably reduce the sensitivity, preventing the ultrasound wave from propagating through material media in steam pipe systems.

In order to meet the requirements of high Curie point and high piezoelectric properties, a modified Navy type II piezoelectric material (known as PZTSA) was selected because this material family offers a combination of high piezoelectric properties and high Curie temperature. Based on the observed results, 2.25 MHz, modified type II, EC-64 piezoelectric material and TRS203 piezoelectric material yield satisfactory probe bandwidth and sensitivity with high thermal stability up to 250° C. EC-64 is available from ITT Exelis—Acoustic Systems, 2645 South 300 West, Salt Lake City, Utah 84115. It is described as follows: This "hard" lead zirconate titanate material was developed for general power applications. Having high electromechanical coupling, high piezoelectric charge constant, and low dielectric loss under high electric driving fields, it is suitable for high power, low frequency broad band projectors, squeeze sensors, spark generators, and other high power electro-acoustic devices.

TRS203 is available from TRS Technologies, Inc., 2820 E. College Avenue, Suite J, State College, Pa. 16801.

The room temperature properties of these piezoelectric materials are listed in Table 1. Although both ceramics showed similar transducer performance below 250° C., TRS 203 ceramics possess higher transition temperature compared to conventional type II ceramics (see FIG. 10), allowing for sensing over a broader temperature range.

TABLE 1

Dielectric and electromechanical properties of EC-64 and TRS203 piezoelectric materials.

| Transducer | $T_C$ (° C.) | $\rho$ (g/cc) | c (m/s) | $k_t$ | $\varepsilon_{33}^T/\varepsilon_o$ | tan$\delta$ | $c_{33}^D$ (GPa) |
|---|---|---|---|---|---|---|---|
| EC-64 | 350 | 7.8 | 4452 | 0.45 | 1116 | 0.02 | 154 |
| TRS203 | 375 | 7.81 | 4547 | 0.45 | 1411 | 0.013 | 161 |

The parameters listed in Table 1 include $T_C$ (Curie Temperature in ° C.), $\rho$ (density in grams/cc), c (speed of sound in meters/second), $k_t$ (coupling coefficient in thickness dimension), $\varepsilon_{33}^T/\varepsilon_o$ (ratio of DC permittivity to electric displacement), tan$\delta$ (dielectric loss factor or loss tangent) and $c_{33}^D$ (elastic stiffness constant).

Figure 10:
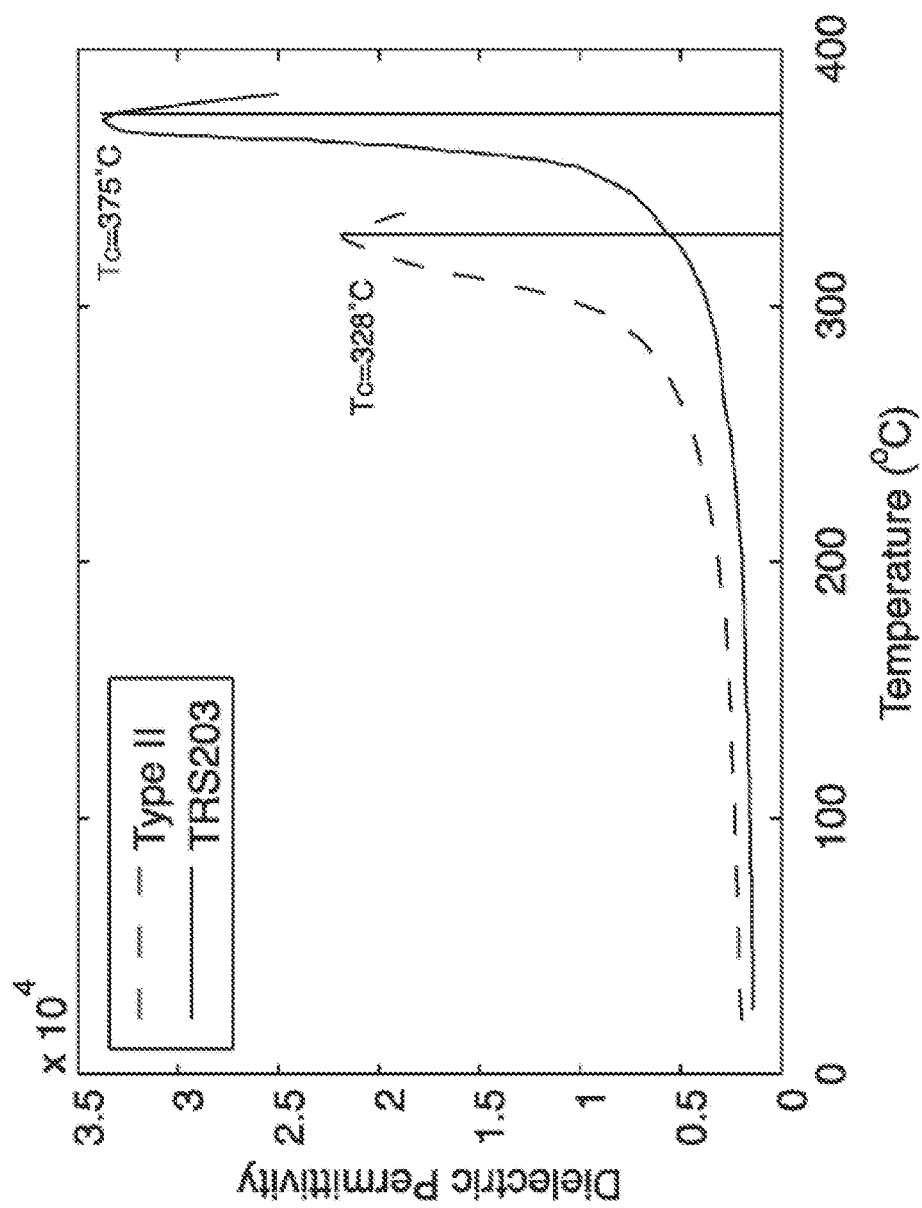
FIG. 10 is a graph that shows the temperature dependent dielectric properties of conventional Type II and TRS203 ceramics.

FIG. 10 is a graph that shows the temperature dependent dielectric properties of conventional Type II and TRS203 ceramics. The data was obtained from TRS Technologies Inc.

In one embodiment, a thick and high impedance layer, referred to as backing, was attached on the back of the piezoelectric transducer. The purpose of this backing is to reduce the duration of the ringing in order to be able resolve shallow water depths and have high resolution. However, an additional consequence is that it lowers the probe sensitivity. Therefore, the appropriate selection of a backing layer is an important factor for the design of successful and efficient ultrasound probes. Three different types of backing were used in this study: (A) a high impedance polymer (e.g., a mixture of 20% of tungsten particles and 80% of high temperature epoxy, available from Duralco 4460, Cotronics Corp., 131 47th Street, Brooklyn, N.Y. 11232), (B) a low impedance polymer (Duralco 4460), and (C) no backing (air backing). The general properties of Duralco 4460 are listed in Table 2.

TABLE 2

| Sample | $T_m$ (° C.) | $\rho$ (g/cc) | c (m/s) | $\alpha$ (*$10^5$ ° C.) | $\eta$ (cps) |
|---|---|---|---|---|---|
| Duralco4460 | 315 | 1.1 | 2200 | 5.4 | 600 |

The parameters listed in Table 2 include $T_m$ (maximum usage temperature), $\rho$ (density), c (longitudinal sound velocity) $\alpha$ (thermal expansion coefficient) and $\eta$ (viscosity).

On the front surface of a piezoelectric material, a thin layer is generally added to protect the transducer surface from the wear and corrosion when the probes are operating directly into high impedance load, such as steel pipe (~40 MRayl). The optimum impedance and ¼ wavelength matching layer thickness of the front layer can be obtained using the following equations:

$$Z_m = \sqrt{Z_t Z_p}, \; t_m = \frac{v_m}{4 f_t} \quad (1)$$

where Z, f, t and v are acoustic impedance, operating frequency, thickness and sound velocity, respectively. The subscripts m, t, and p refer to matching layer, transducer layer and propagating medium, respectively.

Ultrasonic probe was assembled with the piezoelectric transducer attached to a corrosion resistant stainless steel housing using an insulating commercial alumina adhesive paste (Resbond 989-FS, available from Cotronics Corporation of Brooklyn, N.Y.). This ceramic adhesive can provide high bond strength and excellent high temperature electrical, moisture, chemical and solvent resistance up to 1650° C. The transducer was then electrically connected to a RG188 coaxial cable that can sustain temperatures much higher than 250° C. (CB-188LN-100, available from CD International Technology, Inc., 3284 Edward Avenue, Suite C, Santa Clara, Calif. 95054). For soldering the wires, Ersin multi core high temperature solder (Ersin Multicore 366 Solder, available from Henkel Loctite Corporation, 15051 E Don Julian Road, Industry, Calif. 91746) that has melting point of about 400° C. was used. The rear face of the housing was covered with aluminum using high temperature epoxy (Duralco 4460). Images of the fabricated ultrasonic probes that were used for high temperature ultrasonic testing are shown in FIG. 11.

Figure 11:
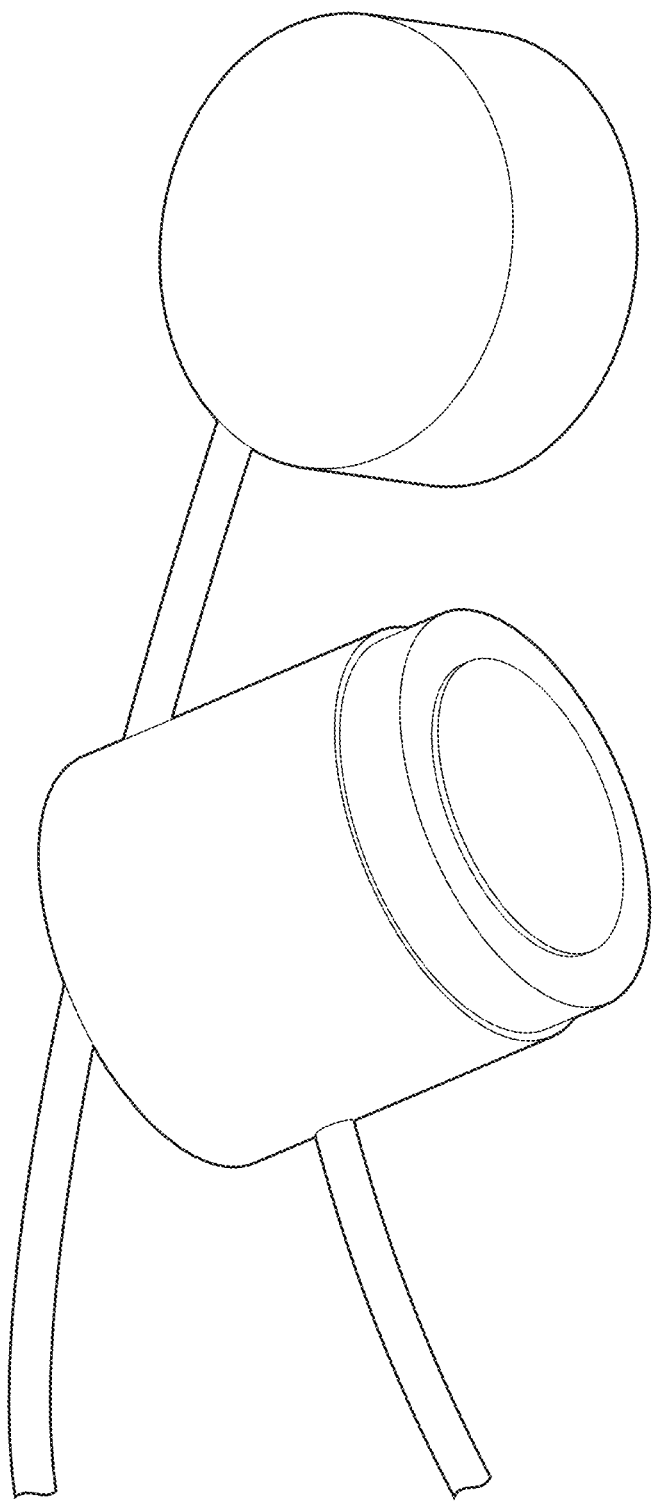
FIG. 11 is an image of two examples of the fabricated thickness mode high temperature piezoelectric probe.

FIG. 11 is an image of two examples of the fabricated thickness mode high temperature piezoelectric probe.

Figures 12A, 12B:
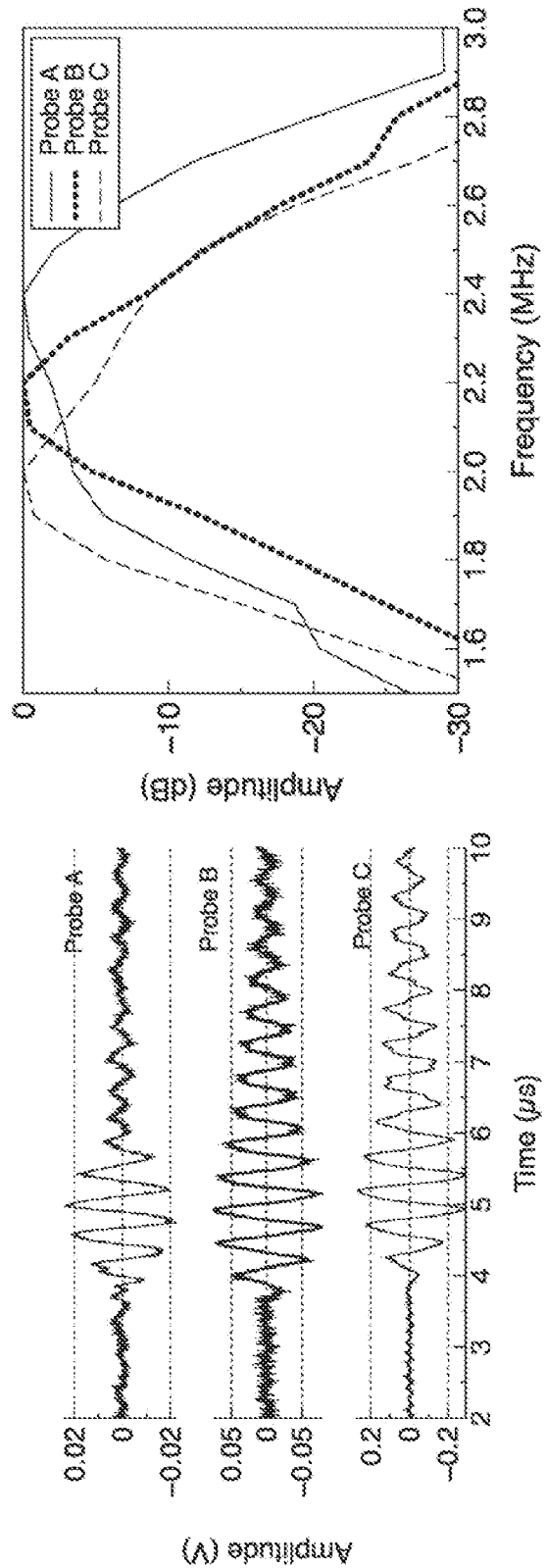
FIG. 12A is a graph of the time-domain pulse-echo responses from a steel reflector in air, using probe A, probe B, and probe C.
FIG. 12B is a graph of the frequency-domain pulse-echo responses from a steel reflector in air, using probe A, probe B, and probe C.

The performance of the fabricated ultrasonic probes was investigated using conventional pulse echo response measurements, in which the fabricated probes were placed in aluminum plate and excited by a Panametrics pulser/receiver (model 5052PR, Panametrics Inc., Waltham, Mass.). Note that the pulser setting is as follows: repetition rate: 4 kHz; energy level: 1; attenuation: 20 and 2 dB step; high-pass filter: 1 MHz; damping level 4; and −20 dB amplifier gain. The pulse echo responses of the probes were recorded by receiving the reflected echo using a Tektronics model TDS2034B oscilloscope. FIG. 12A shows the time domain pulse-echo waveforms and FIG. 12B shows the normalized frequency spectrum for prepared ultrasonic probes A, B and C. Because of a heavy backing ($Z_b$=10 MRayl), probe A shows less ringing compared to probes B and C, leading to high-probe bandwidth on the order of 29.3%. The short pulse of a heavy backed probe is obtained because a heavy backing layer dampens the piezoelectric transducer to shorten the pulse length and ring down. The signal amplitude of probe A is significantly lower than a light backed (B) and air backed probes (C) because a large amount of power is lost in the backing layer. Probe C exhibited the highest signal amplitudes, being on the order of 0.54 $V_{pp}$, which is an order of magnitude higher than that of probe A, whose signal amplitude is around 0.05 $V_{pp}$. However, the pulse length and the bandwidth of the probe were increased and decreased, respectively. The measured properties made from three different ultrasonic probes are summarized in Table 3.

TABLE 3

Measured acoustic performance for various ultrasonic probes.

|  | Probe A | Probe B | Probe C |
|---|---|---|---|
| $Z_b$ (Rayl) | 10M | 2M | 400 |
| $F_C$ (Mhz) | 2.4 | 2.2 | 2 |
| BW (%) | 29.3 | 16.9 | 23.18 |
| $V_{pp}$ | 0.048 | 0.15 | 0.544 |

$Z_b$ is backing material and $F_c$ is center frequency BW is −6 dB bandwidth and $V_{pp}$ is peak-to-peak voltage. $M=10^6$.

Figure 13:
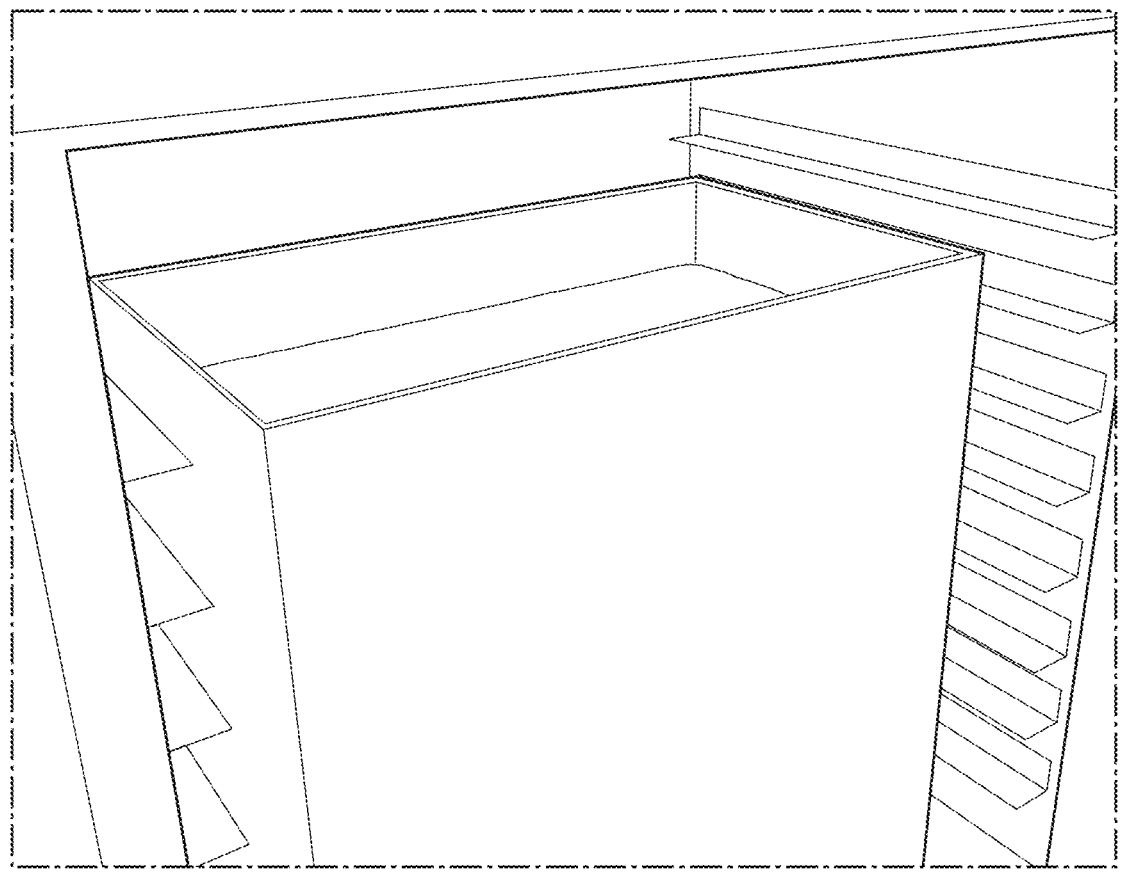
FIG. 13 is an image of the high temperature (HT) test bed with safflower oil where the probe was subjected to 250° C.
Figure 14A:
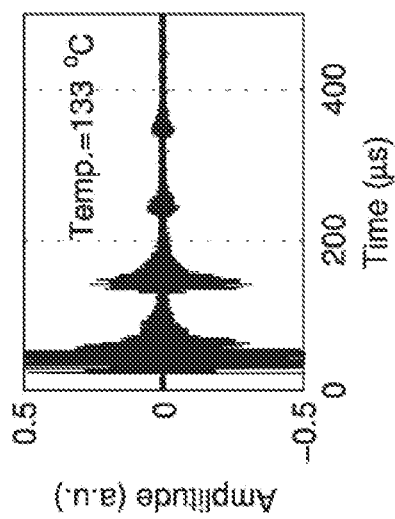
FIG. 14A through FIG. 14F are graphs of pulse-echo responses using an air-backed probe from the half steam pipe that contains silicon oil at various temperatures.
Figure 14B:
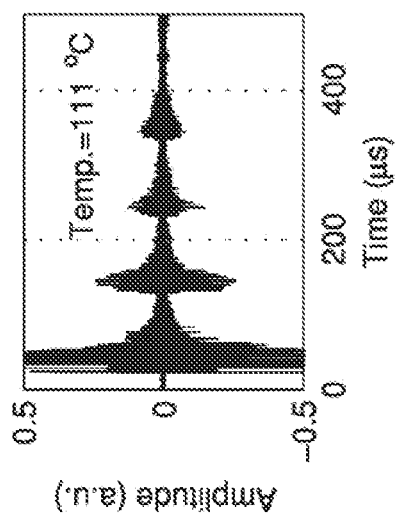
Figure 14C:
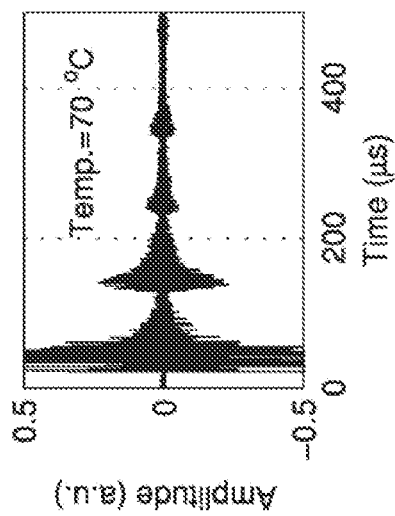
Figure 14D:
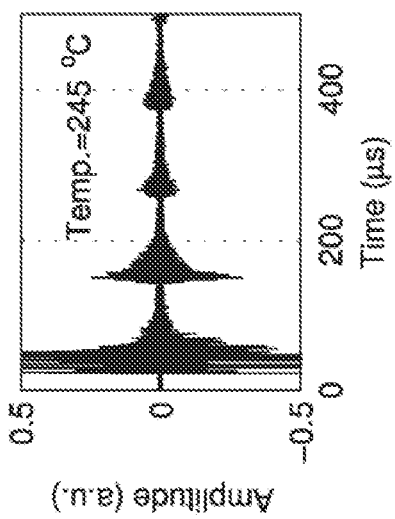
Figure 14E:
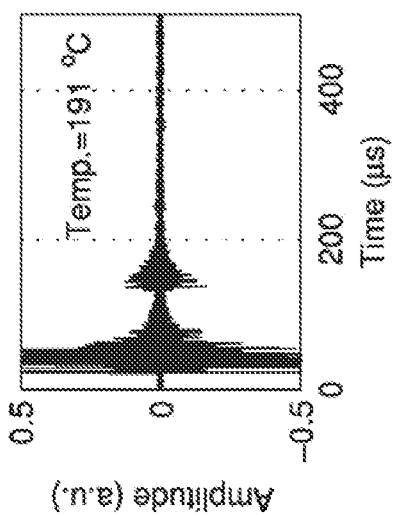
Figure 14F:
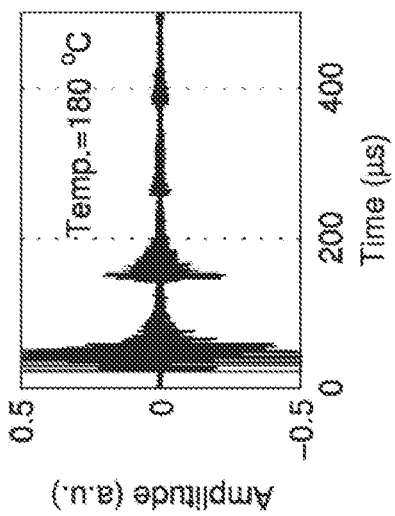

A high temperature chamber (Blue M 6680, Signal Test, Inc. San Diego, Calif.) was used to test the probe and was operated up to 250° C. Because of size limitation of the chamber, a pipe was cut in half along its length and part of the half pipe was used for high temperature testing. A picture of the pipe test bed is shown in FIG. 13. The pipe was filled with silicon oil (Clearco DPDM-400 Diphenyl-Dimethyl Silicone, Clearco Products Co., Inc. Bensalem, Pa.), which is able to sustain the temperatures from −20° C. to 250° C. Silicon oil was used as a substitute for condensed water in order to avoid safety issues related to steam and high pressure. The pulse echo responses of the probes were monitored and recorded by receiving the reflected echo using a LabVIEW-controlled computer. Since the oil has low heat conduction, where the thermal conductivity of the oil is $3.2\times10^4$ cal/cm/s/° C., a thermocouple was inserted into the oil and tracked the temperature as it was increased. The height of the silicon oil was measured while tracking the temperature of the chamber.

FIG. 13 is an image of the high temperature (HT) test bed with safflower oil where the probe was subjected to 250° C.

Various ultrasonic probe configurations were tested to determine the optimum probe design. It was found that the reflected signals from the probe A and B were too low to allow for good height measurement accuracy. This is caused by a non-flat surface of the pipe, resulting in a large energy loss through the pipe wall. In addition, the silicon oil has much higher attenuation of sound compared to water, where the room temperature attenuation ($cm^{-1}$) of water and silicon oil were reported to be $23\times10^{-17}$ $f^2$ and $2\times10^{-12}$ $f^{1.7}$, respectively. In contrast, the air-backed probe showed a significant capability of transmitting and receiving signals through a pipe wall at high temperature resulting from the much higher sensitivities compared to others. The results of pulse-echo response using air-back probe at different temperatures are illustrated in FIG. 14A through FIG. 14F.

FIG. 14A through FIG. 14F are graphs of pulse-echo responses using an air-backed probe from the half steam pipe that contains silicon oil at various temperatures.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A monitoring system for determining the height of fluid in a pipe, comprising:
    an ultrasonic probe, wherein the ultrasonic probe includes
        a piezoelectric transducer element configured to receive and transmit ultrasonic waves,
        electrical input terminals configured to receive a driving signal to said piezoelectric transducer element,
        electrical output terminals configured to provide a response signal from said piezoelectric transducer element; and
    a probe alignment system, configured to align the ultrasonic probe to an exterior wall of the pipe.

2. The monitoring system of claim 1, wherein the piezoelectric transducer element has a Curie temperature of at least 350° C.

3. The monitoring system of claim 1, wherein the piezoelectric transducer element has a dielectric loss tangent (tan δ) of 0.02 or less.

4. The monitoring system of claim 1, wherein the piezoelectric transducer element has an electromechanical coupling factor in thickness dimension (Kt) of at least 0.45.

5. The monitoring system of claim 1, wherein the ultrasonic probe further comprises a backing.

6. The monitoring system of claim 5, wherein the backing is a selected one of air, a high impedance polymer or a low impedance polymer.

7. The monitoring system of claim 1, wherein the ultrasonic probe further comprises a preload flexure, configured to coordinate with the probe alignment system to maintain a preload offset.

8. The monitoring system of claim 1, wherein the ultrasonic probe further comprises:
    a housing,
    a preload flexure, configured to coordinate with the probe alignment system to maintain a preload offset
    a protection layer, and
    a backing,
    wherein
        the housing is a cylindrical housing having a front face configured to mount against the exterior surface of the pipe, and a rear face facing away from the pipe,
        the preload flexure is disposed in the housing at the front surface,
        the piezoelectric element is a round disc, disposed in the preload flexure, with an inner surface attached to the backing, and an outer surface attached to the protective layer.

9. The monitoring system of claim 8, wherein
    the housing contains a corrosion resistant stainless steel,
    the piezoelectric element is fastened to the housing with an alumina adhesive paste, and
    the input electrical terminals and the output electrical terminals are a coaxial cable, soldered onto the piezoelectric element.

10. The monitoring system of claim 1, wherein the probe alignment system comprises:

a transducer alignment fixture configured to align and determine the axis of the ultrasonic probe relative to the surface of the pipe when the ultrasonic probe is inserted into the transducer alignment fixture and mounted to the pipe, and a fastening system to secure the transducer alignment fixture to the pipe.

11. The monitoring system of claim 10, wherein
the transducer alignment fixture includes:
   a frame,
   a probe alignment guide, connected to the frame by way of a plurality of flexures,
   a connection mechanism, configured to connect the frame to the fastening system; and
the fastening system includes:
   a strap, wherein the strap wraps around the pipe and is configured to connect to the transducer alignment fixture via the connection mechanism of the frame.

12. The monitoring system of claim 11, wherein the plurality of flexures are configured to maintain the axis of the ultrasonic probe with respect to the transducer alignment fixture and keep the ultrasonic probe in contact with said steam pipe.

13. The monitoring system of claim 11, wherein the plurality of flexures are parallel to each other.

14. The monitoring system of claim 11, wherein the transducer alignment fixture further comprises at least one alignment bolt, the alignment bolts being connected to the surface of the frame, configured to align the transducer alignment fixture relative to the pipe.

15. The monitoring system of claim 14, wherein said at least one alignment bolt has a sharp end, and connects to the frame at a surface of the frame facing the pipe.

16. The monitoring system of claim 14, wherein said at least one alignment bolt has a cone shape, and connects to the frame at a surface of the frame facing the pipe.

17. The monitoring system of claim 14, wherein said at least one alignment bolt has a position that is capable of being independently adjusted to align the transducer alignment fixture relative to a local preferred direction.

18. The monitoring system of claim 17, wherein the local preferred direction is a local vertical direction.

19. The monitoring system of claim 17, wherein the local preferred direction is normal to a surface of the pipe and a surface of water condensation within the pipe.

20. The monitoring system of claim 11, wherein the connection mechanism is a selected one of a pin joint, a ball joint or a sliding ball joint.

21. The monitoring system of claim 11, wherein the fastening system further includes a tension t-bolt with a spring connected to the strap, configured to maintain tension through the strap.

* * * * *